United States Patent [19]

Rattner

[11] Patent Number: 5,409,446

[45] Date of Patent: Apr. 25, 1995

[54] COUPLING DEVICE FOR INTRODUCING ACOUSTIC WAVES INTO THE BODY OF A LIFE FORM

[75] Inventor: Manfred Rattner, Grossenseebach, Germany

[73] Assignee: Siemens Aktiengesellschaft, Munich, Germany

[21] Appl. No.: 157,134

[22] PCT Filed: Jun. 4, 1992

[86] PCT No.: PCT/DE92/00458

§ 371 Date: Dec. 6, 1993

§ 102(e) Date: Dec. 6, 1993

[87] PCT Pub. No.: WO92/21288

PCT Pub. Date: Dec. 10, 1992

[30] Foreign Application Priority Data

Jun. 6, 1991 [DE] Germany .......................... 4118610.9

[51] Int. Cl.⁶ ............................................. A61B 17/22
[52] U.S. Cl. .......................................... 601/4; 601/2; 607/97; 128/662.03
[58] Field of Search ......................................... 601/2-4; 128/660.01, 660.03, 662.03; 607/97

[56] References Cited

U.S. PATENT DOCUMENTS

| | | |
|---|---|---|
| 3,356,086 | 12/1967 | Behney . |
| 4,105,018 | 8/1978 | Greenleaf et al. . |
| 4,338,948 | 7/1982 | Perez-Mendez et al. ............ 128/660 |

FOREIGN PATENT DOCUMENTS

| | | |
|---|---|---|
| 2610061 | 9/1977 | Germany . |
| 2718847 | 11/1978 | Germany . |
| 3005237 | 8/1981 | Germany . |
| 3119295 | 12/1982 | Germany . |
| 3227624 | 1/1984 | Germany . |
| 3503702 | 8/1986 | Germany ............................... 601/4 |
| 3733439 | 4/1988 | Germany . |
| 3737593 | 5/1988 | Germany . |
| 1052233 | 7/1983 | U.S.S.R. . |

Primary Examiner—Ruth S. Smith
Attorney, Agent, or Firm—Hill, Steadman & Simpson

[57] ABSTRACT

The invention is directed to a coupling device for introducing acoustic waves into the extremity of a life form, said coupling device comprising a rigid, hollow-cylindrical outside part as the entry wall for the acoustic waves, a flexible hose section coaxially arranged in the outside part as the exit wall, and a propagation medium for the acoustic waves which fills the annular space between outside part and hose section.

9 Claims, 1 Drawing Sheet

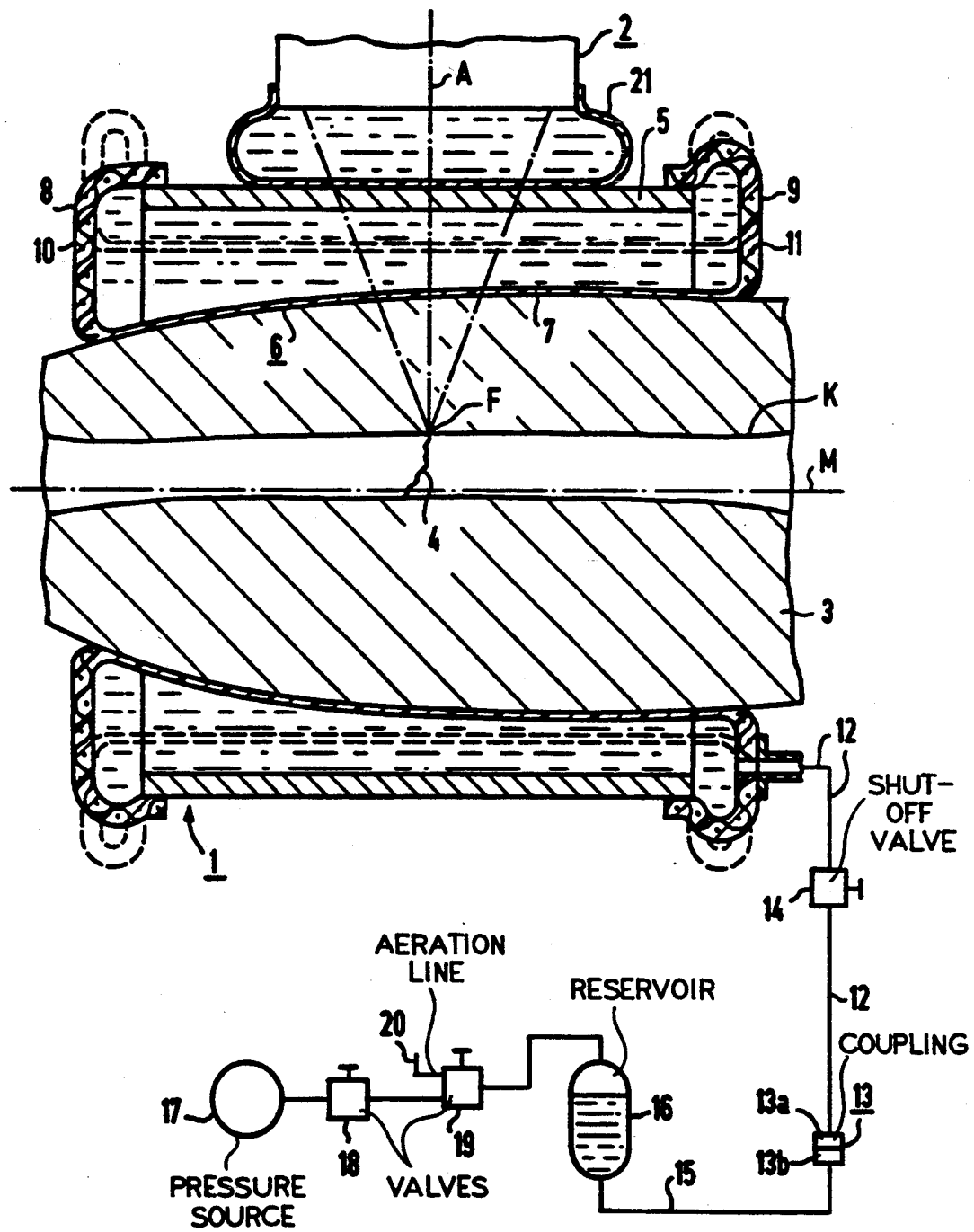

COUPLING DEVICE FOR INTRODUCING ACOUSTIC WAVES INTO THE BODY OF A LIFE FORM

BACKGROUND OF THE INVENTION

1. Field of Invention

The invention is directed to a coupling device for introducing acoustic waves into the body of a life form.

2. Description of the Prior Art

Acoustic waves are introduced into the body of life forms both for diagnostic as well as for therapeutic purposes, such as in apparatuses for ultrasound diagnostics and extracorporeal shock wave lithotripsy (ESWL). The acoustic waves can thereby not be directly introduced into the body of the life form, i.e. on the basis of direct application of the emission surface of the ultrasound transducer or, of the shock wave source against the body surface of the life form. On the contrary, a usually fluid propagation medium for the acoustic waves is generally arranged between the source of the acoustic waves.

For example, it can thus be provided that the source of acoustic waves is introduced into the wall of a bath containing the propagation medium wherein the patient is seated such that the patient assumes the respectively required position relative to the source of the acoustic wave. Apart from the fact that it involves substantial technological outlay, this solution is hygienically problematical. A switch has therefore been made to integrating the source of acoustic waves into a housing filled with the propagation medium, this housing comprising an exit window through which the generated acoustic waves can emerge. The housing containing the source can then be applied against the body surface with its exit window in such a spatial orientation that the diagnostically or, respectively, therapeutically relevant region of the body is charged with the acoustic waves. This solution, which is referred to as "dry coupling", unites the advantage of low technological outlay with that of beneficial hygienic conditions. The exit window, moreover, can be fashioned as a flexible application pillow, with the advantage that a contact area between the exit window and the body surface that is adequately large for the introduction of acoustic waves also derives in body regions wherein parts of the skeleton are located immediately below the body surface.

The problem arises in certain cases that the source of acoustic waves, retaining the "dry coupling" with the body surface, must be particularly automatically adjusted relative to the body with a mechanical adjustment means. For example, this is the case when the focus of the shock waves along the zone to be treated must be adjusted in the treatment of bone conditions in the region of the extremities with focused shock waves, this, for example, potentially making it necessary that the shock wave source be conducted around the extremity in a swivel motion. In these cases, a technologically complicated and expensive adjustment mechanism must be provided for the source of acoustic waves even when the exit window is executed as a flexible application pillow, since it can otherwise not be assured that the contact area between exit window and body surface is adequately large in order to guarantee a good acoustic coupling.

German OS 35 03 702 discloses a "dry" coupling device having an exit window formed by a flexible, stretchable hose section arranged concentrically in the outside part which, together with the outside part, limits an annular space filled with a propagation medium. In this known device, however, the outside part does not constitute an entry wall for the acoustic waves. Instead, the outside part is provided with an opening into which a shockwave source is introduced.

SUMMARY OF THE INVENTION

The invention is based on the object of specifying a coupling device for acoustic waves which makes it possible in a simple and cost-beneficial way to adjust, particularly to automatically adjust a source of acoustic waves relative to the body into which acoustic waves are to be introduced given "dry coupling" upon constant retention of a good acoustic coupling.

This object is inventively achieved by a coupling device for introducing acoustic waves into the body of a life form which comprises:

a) an entry wall for the acoustic waves which is formed by an outside part comprising a rigid, rotationally symmetrical, outer surface;

b) an exit wall for the acoustic waves which is formed by a flexible, stretchable hose section concentrically arranged in the outside part, whereby the hose section together with the outside part limits an annular space; and c) a propagation medium contained in the annular space for the acoustic waves.

As a consequence of the fact that the outer surface of the entry wall is fashioned rotationally symmetrical, the source of the acoustic waves can be conducted around the coupling device on a circular path and, for example, around an extremity accepted therein and on a circular path around that axis with respect whereto the outer surface is rotationally symmetrical, without having the contact area of the exit window or, coupling cushion of the source of acoustic waves to the outer surface of the entry wall changing to a noteworthy degree. As a consequence of the fashioning of the exit wall as a flexible hose section, moreover, it is guaranteed that this lies flush against the entire circumference of the body or, respectively, body part into which the acoustic waves are to be introduced. It thus becomes clear that, first, a good acoustic coupling is always assured between the coupling cushion of the source of acoustic waves and the entry wall of the coupling device and, on the other hand, between the exit wall of the coupling device and the body or body part, so that the acoustic waves can be introduced into the body or into the body part with the lowest possible losses. Moreover, the adjustment of the source of acoustic waves relative to the body or to the body part takes on an extremely simple configuration since this—as a consequence of the interposition of the coupling device comprising a rotationally symmetrical, outer surface—can ensue on a circular path, which substantially simplifies an automatic adjustment of the source of the acoustic waves.

It is provided in a preferred embodiment of the invention that the outer surface of the outside part is cylindrically fashioned. On the basis of combining a circular motion around the center axis of the generated surface and a straight-line motion parallel to the center axis of the generated surface, it then becomes possible in a simple way to align the source of acoustic waves nearly arbitrarily relative to the body or, respectively, body part accepted in the coupling device within the limits established by the dimensions of the coupling device.

In the preferred embodiment the volume of the annular space and the quantity of propagation medium contained therein are variable. The inside diameter of the hose section provided as exit wall can thus be varied by varying the amount of propagation medium contained in the annular space, this yielding the advantage that the flush application of the hose section against the surface of the body or of the body part required for a good acoustic coupling can always be realized for bodies or body parts having different circumferences.

In order to keep the acoustic losses that arise due to the insertion of the coupling device between the source of acoustic waves and the body or the body part as low as possible, one version of the invention provides that the acoustic impedances of the propagation medium, of the material of the outside part and of the material of the hose section at least essentially coincide. No noteworthy losses due to reflection then arise at the boundary surfaces between outside part and propagation medium and between propagation medium and hose section. The losses can be further reduced when the acoustic impedances of the propagation medium, the material the outside part and of the material of the hose section at least essentially coincide with that of animal, particularly human tissue, since no noteworthy reflections then occur either at the boundary surface between the hose section and the surface of the body or body part. Acoustic impedances that largely coincide with human tissue are present when water is provided as acoustic propagation medium, at least one material from the group of ethylene-propylene-diene and polymethylene—EPDM—rubber, polymethylpentene (TPX), polystyrol is provided as material of the outside part and at least one material from the group of EPDM rubber, Latex, polyvinylchloride (PVC) is provided as material of the hose section.

DESCRIPTION OF THE DRAWINGS

An exemplary embodiment of the invention is shown in a highly schematic longitudinal section in the attached drawing.

DESCRIPTION OF THE PREFERRED EMBODIMENTS

The coupling device of the invention shown in the figure and referenced 1 overall serves the purpose of acoustically coupling a schematically indicated shock wave source 2 for the treatment of a bone condition, for example a poorly healing fracture due to inadequate callus formation, to a human extremity 3, for example a thigh. For treatment, focused shock waves generated with the shock wave source 2 (as used herein "shockwaves"0 means acoustic pressure pulses having an extremely steep leading edge) are introduced into the extremity 3 through the coupling device 1. As exit window for the shock waves, the shock wave source 2 comprises a flexible application cushion 21 pressing against the coupling device 1. For example, U.S. Pat. No. 4,674,505 discloses such a shock wave source. For treating the fracture, the focus F of the shock waves must be moved along the fracture gap 4 of the fracture. The bone K to be treated is shown unsectioned in the figure.

As the entry wall for the shock waves, the coupling device 1 of the invention comprises a rigid, cylindrical tube-shaped outside part 5 that is fabricated of a material, for example EPDM rubber, polymethylpentene (TPX) or polystyrol whose acoustic impedance essentially corresponds to that of human tissue and that only slightly attenuates the shock waves. Further, the coupling device 1 comprises a flexible hose part 6 that is manufactured of a stretchable material, for example EPDM rubber, Latex or polyvinylchloride (PVC) that only slightly attenuates shock waves and has an acoustic impedance essentially corresponding to that of human tissue. As the exit wall for the shock waves, the hose part 6 comprises a hose section 7 each of whose ends merges into a radially outwardly extending bead part 8, 9, whereby the free edges of the bead parts 8, 9 of the hose part 6 are connected liquid-tight, for example by gluing, to the outside part 5 along the respectively corresponding edge of the cylindrical, outer generated surface of the outside part 5. The hose part 6 has an increased wall thickness in the region of the bead parts 8, 9. A schematically indicated fabric 10, 11 that can be fabricated, for example, of nylon thread is also respectively embedded into the bead parts 8, 9. What is thereby achieved is that the hose part 6 is in fact flexible but not stretchable in the region of the bead parts 8, 9.

The annular space limited by the outside part 5 and by the hose part 6 having the hose section 7 and the bead parts 8, 9 is filled with a fluid as propagation medium for the shock waves generated with the shock wave source 2, the acoustic impedance thereof essentially corresponding to that of human tissue. For example, water is suitable as propagation medium. In order to be able to fill the annular space with water, a hose 12 is attached to the bead part 9, the end of said hose 12 being provided with a schematically indicated coupling part 13a and a schematically illustrated shut-off valve 14 being connected therein. The coupling part 13a is a component of a coupling 13 whose second coupling part 13b is provided at the end of a line 15 that leads to a reservoir 16 containing water which, as the line 15, is schematically shown. The space located above the water level in the reservoir 16 is in communication with a schematically indicated pressure source 17, for example a compressed air bottle, and can be charged with a valve 18 with an adjustable pressure that is elevated in comparison to the ambient pressure. A further valve 19, which is schematically shown as is the valve 18, is connected between the pressure source 17 and the reservoir 16, this further valve 19 making it possible to optionally connect the interior of the reservoir 16 to the pressure source 17 or to the surrounding atmosphere via an aeration line 20.

For the implementation of a treatment, the hose 12 is first connected by the coupling 13 to the unpressurized reservoir 16 and the shut-off valve 14 is opened. Insofar as the water located in the annular space is under a pressure which is elevated in comparison to the ambient pressure, this water flows into the reservoir 16. This leads to the fact that the hose part 6 assumes its initial shape indicated with broken lines in the figure, the hose section 7 therein having a hollow-cylindrical shape and the bead parts 8, 9 having an approximately U-shape in cross section. The extremity 3 to be treated is now introduced into the coupling device 1 or the coupling device 1 is pushed onto the extremity 3 to be treated. When, differing from what is shown in the figure, the extremity 3 to be treated has an outside diameter that is larger than the inside diameter of the hose section 17 in its initial shape, water is thereby expressed back into the reservoir 16. For improving the acoustic coupling, the extremity 3 to be treated can potentially be coated with a water-containing gel before the application, as is likewise employed in the implementation of ultrasound examinations. When the extremity 3 assumes the desired position in the coupling device 1, the fracture as viewed in longitudinal direction of the extremity 3 being preferably located centrally between the ends of the coupling device 1 in this desired position, the reservoir 16 is charged with a pressure matched to the respective treatment by an appropriate actuation of the valve 20, this pressure being adjustable with the valve 18. Water is thereby pressed from the reservoir 16 into the annular space, with the result that the flexible and stretchable hose section 7 of the hose part 6 presses flush against the extremity 3. When the desired pressure is present, the coupling 13 can be released after the closing of the shut-off valve 14 and after the reservoir 16 has been switched unpressurized with the valve 20 and the extremity 3 to be treated can be seated such that the coupling device 1 is accessible to the shock wave source 2 in the region of the entire, outer generated surface of the outside part 5. It is thereby expedient when the coupling device 1 is fixed in the corresponding position with the assistance of retainer means and in a way that is not shown. In this position, the shock wave source 2 has its flexible application cushion 21 pressing against the outer surface of the outside part 5 of the coupling device 1, whereby it is expedient to coat the application cushion 21 and/or the outer surface of the outside part 5 with a water-containing gel for improving the glide behavior and the acoustic coupling.

Since it has been shown that charging a fracture with focused shock waves induces callus formation or bone growth, the focus F of the shock waves generated with the shock wave source 2 is moved along the entire fracture gap 4 for treating the fracture. To this end, the shock wave source 2, with a constant emission of shock waves, is gradually moved around the extremity 3 with constant application of the application cushion 21 against the outer surface of the outside part 5. It must thereby be simultaneously assured on the basis of corresponding, additional adjustment motions that the focus F of the shock waves is always essentially located in the region of the boundary surface between the bone and the tissue surrounding it. In the case of the coupling device of the invention, this can be achieved in a technologically simple way. Since the outer surface of the outside part 5 of the coupling device 1 is cylindrically fashioned, namely, it is assured that the acoustic axis A of the shock wave source 2 on which the focus F of the shock waves lies always intersects the center axis M of the coupling device 1 during the treatment. On the basis of a simple circular motion of the shock wave source around the center axis M and on the basis of a likewise simple, straight-line displacement of the shock wave source parallel to the center axis M, it can thus be achieved that the acoustic axis A intersects the fracture gap 4 for arbitrary positions of the shock wave source 2 on the circular path. In order to guarantee that the focus F of the shock waves lies in the boundary surface between bone and surrounding tissue in the required way, the focus F must merely be displaced as required in a known way along the acoustic axis A. It thus becomes clear that the coupling device 1 of the invention makes it possible to adjust the focus F of the shock waves along the fracture gap 4 on the basis of adjustment motions of the shock wave source 2 that can be technologically realized in a simple way. This occurs with the assistance of a locating means (not shown in the figure) that can operate on an x-ray and/or ultrasound basis in a known way. The acoustic coupling of the shock wave source 2 to the extremity 3 to be treated is always of the same quality regardless of the position of the shock wave source 2 relative to the extremity 3 since, on the one hand, the contact area between the application cushion 21 of the shock wave source 2 and the coupling device 1 is always of the same size as a consequence of the cylindrical shape of the outer surface of the outside part 5 and, on the other hand, a flush application of the coupling device 1 against the extremity to be treated is always assured as a consequence of the flexible and elastic properties of the hose section 7.

The outer surface of the outside part 5 need not necessarily be cylindrically fashioned. Other rotationally symmetrical shapes, for example a spherical shape, also come into consideration.

The exemplary embodiment which has been set forth is directed to the treatment of a bone condition. The coupling device of the invention, however, can also be employed in other therapeutic and/or diagnostic medical procedures.

We claim as our invention:

1. Coupling device for use with means for generating acoustic waves for introducing said acoustic waves into the body of a life form, comprising:
   a) an entry wall for acoustic waves formed by an entry wall part having a rigid, rotationally symmetrical, outer surface adapted to abut said means for generating acoustic waves;
   b) an exit wall for the acoustic waves formed by a flexible, stretchable hose section concentrically arranged within the entry wall part, and sidewalls connecting said hose section and said entry wall part, the hose section together with the entry wall part and said sidewalls limiting an annular space therebetween; and
   c) a propagation medium for the acoustic waves contained in the annular space, said entry wall, said propagation medium and said exit wall being oriented relative to each other and to said means for generating acoustic waves and to the body of said life form so that said acoustic waves pass sequentially through said entry wall said propagation medium and said exit wall when propagating from said means for generating acoustic waves to the body of said life form.

2. Coupling device according to claim 1, wherein the outer surface of the outside part is cylindrical.

3. Coupling device according to claim 1 or 2, further comprising means for varying the volume of the annular space and the amount of propagation medium contained therein.

4. Coupling device according to claim 1, wherein the propagation medium, the material of the outside part, and the material of the hose section have respective acoustic impedances, said acoustic impedances being substantially the same.

5. Coupling device according to claim 4, wherein the acoustic impedances of the propagation medium, the material of the outside part, and the material of the hose section are substantially the same as human tissue.

6. Coupling device according to claim 1, wherein the propagation medium consists of water.

7. Coupling device according to claim 1 wherein said outside part consists of at least one material selected from the group consisting of ethylene-propylene-diene and polymethylene (EPDM) rubber, polymethylpentene (TPX), and polystyrol.

8. Coupling device according to claim 1 wherein said hose section consists of at least one material selected from the group consisting of ethylene-propylene-diene and polymethylene (EPDM) rubber and polyvinylchloride (PVC).

9. An apparatus for treating a life form with acoustic waves comprising:

a shockwave source having an exit window, said shockwave source generating shockwaves which exit said shockwave source through said exit window; and coupling means for coupling said shockwaves from said exit window of said shockwave source into the body of said life form, said coupling means including an entry wall for the acoustic waves adapted for abutment against said exit window of said shockwave source, said entry wall being formed by a part having a rigid, rotationally symmetrical outer surface, an exit wall for the acoustic waves formed by a flexible, stretchable hose section concentrically arranged within said part of said entry wall and connected thereto by sidewalls, the hose section together with the part of the entry wall and the sidewalls limiting an annular space therebetween, and a propagation medium for the acoustic waves contained in the annular space, said entry wall, said propagation medium and said exit wall being oriented relative to each other and to said shockwave source and to the body of said life form so that acoustic waves pass sequentially through said entry wall, said propagation medium and said exit wall when propagating from said exit window to the body of said life form.

* * * * *